(12) United States Patent
Balijepalli et al.

(10) Patent No.: US 8,759,416 B2
(45) Date of Patent: Jun. 24, 2014

(54) HINDERED PRIMARY CHLORINATED AMINE IN A LATEX FORMULATION

(71) Applicants: Dow Global Technologies LLC, Midland, MI (US); Rohm and Haas Company, Philadelphia, PA (US)

(72) Inventors: Sudhakar Balijepalli, Midland, MI (US); Douglas Hawkins, Maple Glen, PA (US); Kathleen Manna, Quakertown, PA (US); Ian Tomlinson, Midland, MI (US)

(73) Assignees: Dow Global Technologies, LLC, Midland, MI (US); Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 13/671,641

(22) Filed: Nov. 8, 2012

(65) Prior Publication Data

US 2013/0123386 A1    May 16, 2013

Related U.S. Application Data

(60) Provisional application No. 61/560,442, filed on Nov. 16, 2011.

(51) Int. Cl.
*C09D 5/16* (2006.01)

(52) U.S. Cl.
USPC ............ 523/122; 564/114; 564/118; 564/463

(58) Field of Classification Search
None
See application file for complete search history.

(56) References Cited

U.S. PATENT DOCUMENTS

| | | | | |
|---|---|---|---|---|
| 5,182,327 | A | * | 1/1993 | Biale ............................. 524/556 |
| 5,728,206 | A | * | 3/1998 | Badejo ........................... 106/493 |
| 7,612,126 | B2 | * | 11/2009 | Roschmann et al. ......... 523/201 |
| 2003/0209165 | A1 | | 11/2003 | Gernon et al. |
| 2007/0049642 | A1 | * | 3/2007 | Singleton et al. ............. 514/612 |
| 2007/0224161 | A1 | | 9/2007 | Sun et al. |
| 2008/0268189 | A1 | | 10/2008 | Sun et al. |

FOREIGN PATENT DOCUMENTS

| | | |
|---|---|---|
| WO | 2010019723 A1 | 2/2010 |
| WO | 2011097324 A1 | 8/2011 |

OTHER PUBLICATIONS

Roberts, John T.; Rittberg, Barry R.; Kovacic, Peter From Journal of Organic Chemistry (1981), 46(21), 4111-15 Chemistry of N-halo compounds. 33. Pyrolytic eliminations from N,N-dichloro derivatives of primary, secondary, and tertiary alkyl primary amines.*

Francavilla, Charles, et al. Quaternary ammonium N,N-dichloroamines, as topical, antimicrobial, Bioorganic & Medical Chemistry Letter 19 (2009) 2731-2734.

Cao, Zhengbing, et al."Polymeric N-Halamine Latex Emulsions for Use in Antimicrobial Paints", Applied Materials & Interfaces, vol. 1, No. 2, (2009) 494-504.

* cited by examiner

*Primary Examiner* — Nicole M Buie-Hatcher
*Assistant Examiner* — Chelsea M Lowe
(74) *Attorney, Agent, or Firm* — Reid S. Willis

(57) ABSTRACT

The present invention relates to a process comprising adding a sufficient amount of a halamine with a latex binder to achieve microbial prophylaxis, wherein the halamine is characterized by the following formula:

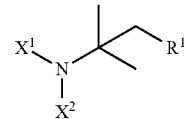

wherein $X^1$ is H, Br, or Cl; $X^2$ is Br or Cl; and $R^1$ is H or a $C_{1-30}$ alkyl group or mixtures thereof. The present invention also relates to a composition comprising the halamine and a latex binder. The present invention provides a quick kill shelf stable preservative for latex binders and for formulations that use such binders.

10 Claims, No Drawings

HINDERED PRIMARY CHLORINATED AMINE IN A LATEX FORMULATION

BACKGROUND OF THE INVENTION

The present invention relates to hindered chlorinated primary amines, which are useful as preservatives for latex formulations.

There is an ongoing need to improve latex preservation; in spite of the availability of well-developed biocide packages in latex products, microbial spoilage still occurs. Although the rate of catastrophic spoilage is low, each event diminishes consumer relationships and confidence.

In addition to preserving a microbe-free environment for latexes in final formulated products, there is a need to improve the efficiency of cleaning the interior surfaces of pipes, vessels, and process equipment without disassembly. This so-called "clean-in-place" technology often includes a sanitize cycle to reduce bacterial contamination using a biocide such as a hypochlorite or an isothiazolone, which kill microbes quickly and completely. Isothiazolones such as KATHON™ Preservatives (A Trademark of The Dow Chemical Company or its Affiliates) are especially attractive because they show a broad spectrum of biocidal activity as well as efficacy at low ppm levels.

On the other hand, isothiazolones tend to have relatively short shelf-life stability (4-6 months), requiring more frequent addition of isothiazolones or bleach to preserve the integrity of the latex. However, bleach and other chlorine-based oxidants are known to adversely impact the properties of the latex and, over time, the integrity of the vessel containing the latex. Furthermore, the activity of bleach and other chlorine based oxidants is limited due to the quick release of chlorine.

Chlorinated hindered amines have recently been proposed as anti-microbial agents for latex paint formulations. For example, Cao et al. discloses the synthesis of N-chloro-2,2,6,6-tetramethyl-4-piperidinyl methacrylate (Cl-TMPM) and its subsequent conversion to the latex polymer polyCl-TMPM, which is described as being useful as a biocide for latex paints. (Cao, Z; Sun, Y; *ACS Appl. Mater. Interfaces*, 2009, 1(2), 494-504). Paints formulated with polyCl-TMPM were found to provide potent long-lasting (>1 year) antimicrobial activities against a wide range of bacteria and to prevent biofilm formation and development. Nevertheless, paints required 1 to 20 weight percent of the latex biocide to achieve quick kill. Consequently, the high levels of additive would be expected to have an adverse impact on the properties and cost of the paint.

Accordingly, it would be desirable to find alternative biocides or biocide packages that have quick kill capability at low concentrations and long shelf stability without adversely affecting the integrity of materials of construction of vessels. It would further be desirable to find inexpensive packages that do not require the development of new biocidal actives that would be subject to costly and time-consuming approval by regulatory agencies.

SUMMARY OF THE INVENTION

The present invention addresses a need by providing, in a first aspect, a process comprising contacting a sufficient amount of a halamine with a latex binder to achieve microbial prophylaxis, wherein the halamine is characterized by the following formula:

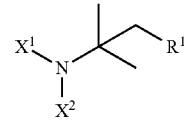

wherein $X^1$ is H, Br, or Cl; $X^2$ is Br or Cl; and $R^1$ is a $C_{1-30}$ alkyl group.

In a second aspect, the present invention is a composition comprising a latex binder and a halamine characterized by the following formula:

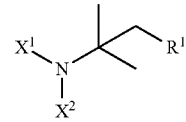

wherein $X^1$ is H, Br, or Cl; $X^2$ is Br or Cl; and $R^1$ is H or a $C_{1-30}$ alkyl group.

The present invention addresses a need in the art by providing a quick kill shelf stable preservative for latex binders and for formulations that use such binders.

DETAILED DESCRIPTION OF THE INVENTION

In a first aspect, the present invention is a process comprising contacting a sufficient amount of a halamine with a latex binder to achieve microbial prophylaxis, wherein the halamine is characterized by the following formula:

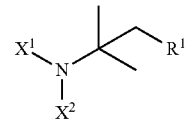

wherein $X^1$ is H, Br, or Cl; $X^2$ is Br or Cl; and $R^1$ is H or a $C_{1-30}$ alkyl group. Preferably, $X^1$ is H or Cl and $X^2$ is Cl. $R^1$ is preferably a $C_{4-20}$ alkyl group or mixtures thereof. As used herein, the term "alkyl group" refers to a linear, branched, or cyclic alkyl group or combinations thereof, preferably linear or branched or combinations thereof. The term "microbial prophylaxis" is used herein to refer to both the destruction of microbes and prevention of microbial build-up.

Examples of preferred suitable halamines are mono- and dichloromines, as illustrated:

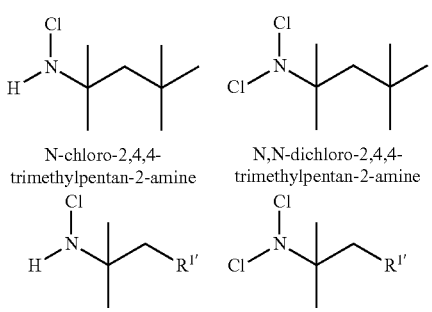

N-chloro-2,4,4-trimethylpentan-2-amine

N,N-dichloro-2,4,4-trimethylpentan-2-amine where $R^{1'}$ is a $C_{8-10}$ linear or branched alkyl group or mixtures thereof; or a $C_{14-20}$ linear or branched alkyl group or mixtures thereof. All of these compounds can be prepared by the chlorination of the corresponding unchlorinated amines. It is preferred that the method of chlorination use a chlorinating agent that is approved as a biocide by the appropriate regulatory agency. For example, the compounds N-chloro-2,4,4-trimethylpentan-2-amine(monochloro-t-octyl amine or Cl-TOA) and N,N-dichloro-2,4,4-trimethylpentan-2-amine(dichloro-t-octyl amine or $Cl_2$-TOA) can be prepared by the chlorination of 2,4,4-trimethylpentan-2-amine (commercially available as PRIMENE™ TOA Amine, a Trademark of The Dow Chemical Company or its Affiliates) in accordance with the following general scheme:

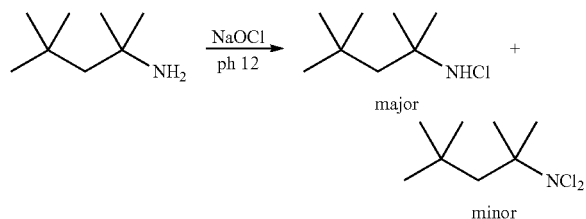

The dichloroamine can be prepared as the major product when the starting material is added to a solution of NaOCl buffered to pH 6.5 with $KH_2PO_4$.

Mono- or dichloroamines or mixtures thereof may also be prepared by contacting the starting amine with sodium dichoroisocyanurate in a biphasic system at ambient or elevated temperatures and with rigorous stirring. Examples of suitable biphasic systems are water and chloroform or water and methylene chloride. It is understood that the halamine may be contacted with the latex either directly or as a mixture of amine and chlorinating agent, which form the halamine in situ.

The halamine, preferably the mono- or dichloroamine or mixtures thereof, is used at various levels depending upon the available halogen, preferably chlorine, in the molecule ($C_8$-chloroamines have twice the available chlorine as $C_{16}$-chloroamines) and the target microbe, but is generally in the range of 10 ppm to 1 weight percent, preferably in the range of 100 to 1000 ppm, based on the volume of the latex. The halamine is preferably added to the latex as a emulsified mixture, for example, as a mixture of 1:1 sodium lauryl sulfate (SLS): halamine to 1:3 sodium lauryl sulfate (SLS):halamine. The particle sizes of the pre-emulsified mixture are generally in the range of 100 nm to 1000 nm.

The nature of the latex binder, which is the film forming component of paint, is not critical. Examples of latex binders include aqueous dispersions of acrylics, styrene-acrylics, vinyl acrylics, and vinyl acetate/ethylene (VAEs). The halamine can be combined with a latex binder stored in a vessel, or combined with a paint formulation in a container. An example of a suitable acrylic latex binder is a butyl acrylate/methyl methacrylate/methacrylic acid binder stabilized with a surfactant such as sodium lauryl sulfate.

Although the halamine is useful as a biocide, it can also be used as a co-biocide with a non-halamine biocide, which can be added to the latex binder prior to, concurrent with, or subsequent to the addition of the halamine. An example of a class of non-halamine biocides is isothiazolones. Examples of suitable isothiazolones include 1,2-benzisothiazol-3(2H)-one, 5-chloro-2-methyl-4-isothiazolin-3-one and 2-methyl-4-isothiazolin-3-one or a combination thereof Examples of commercially available isothiazolones include KATHON™ Preservatives (A Trademark of The Dow Chemical Company or Its Affiliates) and Proxel BIT Preservatives.

In another aspect, the present invention is a composition comprising a latex binder and a halamine characterized by the following formula I:

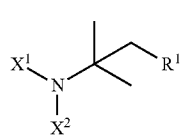

I wherein $X^1$ is H, Br, or Cl; $X^2$ is Br or Cl; and $R^1$ is H or a $C_{1-30}$ alkyl group or mixtures thereof. Preferably, $X^1$ is H or Cl and $X^2$ is Cl; and $R^1$ is —$C(CH_3)_3$ or a $C_{8-20}$ alkyl group or mixtures thereof. Preferably, the composition of the present invention further includes a non-halamine biocide, such as an isothiazolone. As used herein, the term "non-halamine biocide" refers to a biocide that is different from the halamine of formula I.

Preferably, the concentration of the halamine is in the range of 10 ppm to 1% and concentration of the non-halamine biocide is in the range of 1 ppm to 500 ppm based on the volume of the latex binder.

It is observed that halamines retain efficacy even as they revert back to their corresponding unhalogenated amines. Though not bound by theory, it is believed that these unhalogenated amines, though possessing no biocidal properties themselves, act to disrupt the lipid membrane of the microbe, thereby increasing the permeability of any biocidal agents present in the environment. Therefore, the halamines would be expected to exhibit the dual benefit of longer shelf-stability and increased potency in the presence of any other non-halamine biocide.

The composition of the present invention provides shelf stable latex binder that is resistant to microbe formation and is especially useful for clean-in-place applications. The latex binder is useful in coating formulations such as paints, which may include any of a number of suitable components including solvents; fillers; pigments, such as titanium dioxide, mica, calcium carbonate, silica, zinc oxide, milled glass, aluminum trihydrate, talc, antimony trioxide, fly ash, and clay; polymer encapsulated pigments, such as polymer-encapsulated or partially encapsulated pigment particles such as titanium dioxide, zinc oxide, or lithopone particles; polymers or polymer emulsions adsorbing or bonding to the surface of pigments such as titanium dioxide; hollow pigments, including pigments having one or more voids; dispersants, such as aminoalcohols and polycarboxylates; surfactants; defoamers;

flow agents; leveling agents; and additional neutralizing agents, such as hydroxides, amities, ammonia, and carbonates.

EXAMPLES

The following examples are for illustrative purposes only and are not intended to limit the scope of the invention.

Example 1

Preparation of a Heat Aged Latex Binder with Cl-TOA

A 20.0-g dispersion of N-chloro-2,4,4-trimethylpentan-2-amine, 18% sodium lauryl sulfate, and water (Cl-TOA, 0.47 g; SLS, 1.29 g; $H_2O$, 18.24 g) with a particle size in the range of 100 to 850 nm was added to a butyl acrylate/methyl methacrylate/methacrylic acid latex binder (180 g; 50/49/1 percentages by weight) stabilized by SLS (1 weight percent) and Disponil FES 32 emulsifier (1 weight percent). The Cl-TOA/binder preparation was heat aged at 50° C. for 14 days. The concentration of Cl-TOA prior to the heat aging step was 2350 ppm (14 mM). The concentration of Cl-TOA after the heat-aging step was measured by GC to be ~160 ppm based on the volume of the binder.

Example 2

Preparation of a Heat Aged Latex Binder with Cl-TOA and Isothiazolone Preservative The procedures were carried out substantially as described for Example 1 except that, after heat-aging, a diluted sample of KATHON™ LX Microbicide Concentrate (A Trademark of The Dow Chemical Company or Its Affiliates) was mixed in with the binder/Cl-TOA preparation by shaking the samples at 200 rpm for 20 min, giving a final dosage of ~5 ppm active. The concentration of Cl-TOA after the heat-aging step was measured by GC to be ~160 ppm based on the volume of the binder.

Example 3

Preparation of a Heat Aged Latex Binder with Cl-TOA and Isothiazolone Preservative The procedure of Example 2 was repeated except that the constituents of the added dispersion were Cl-TOA (0.19 g), SLS (0.52 g), and water (19.29 g). The concentration of Cl-TOA after the heat-aging step was estimated to be ~65 ppm based on the volume of the binder.

Example 4

Preparation of a Heat-Aged Latex Binder with TOA and Isothiazolone Preservative

A 20.0-g dispersion of 2,4,4-trimethylpentan-2-amine, 18% sodium lauryl sulfate, and water (TOA, 0.38 g; SLS, 1.06 g; $H_2O$, 18.56 g) with a particle size in the range of 100 to 850 nm was added to a butyl acrylate/methyl methacrylate/methacrylic acid latex binder (180 g; 50/49/1 percentages by weight) stabilized by SLS (1 weight percent) and Disponil FES 32 emulsifier (1 weight percent). The TOA/binder preparation was heat aged at 50° C. for 14 days. The concentration of TOA before heat aging was 1900 ppm (14 mM), and GC measurements indicated no change in TOA concentration as a result of heat aging. After heat-aging, a diluted sample of KATHON™ LX Microbicide Concentrate (A Trademark of The Dow Chemical Company or Its Affiliates) was mixed in with the TOA/binder preparation by shaking the samples at 200 rpm for 20 min, giving a final dosage of ~5 ppm active.

Comparative Example 1

Preparation of a Latex Binder with a Non-Halamine Preservative

A diluted portion of KATHON™ LX Microbicide Concentrate was added to a heat-aged butyl acrylate/methyl methacrylate/methacrylic acid latex binder (10 g; 50/49/1 percentages by weight) stabilized by SLS (1 weight percent) and Disponil FES 32 emulsifier (1 weight percent), to a final dosage level of ~5 ppm.

The samples prepared in accordance with Examples 1-4 and Comparative Example 1 were subjected to preservative efficacy testing in accordance with the following procedure:

A 1-g aliquot was removed from each sample and submitted for biocide analysis by a standard HPLC procedure to check the amount of isothiazolone microbicide dosed. The samples were then dosed with the standard industrial inoculum at a level of 0.1 mL/10 g.

Preparation of the Inoculum

All bacteria and yeast were stored at –70° C. to –80° C. in broth and glycerol (15%) prior to inoculum preparation. Molds were maintained on potato dextrose agar (PDA) plates at 2-5° C. The bacteria and yeast cultures were thawed and 0.1-mL aliquots of each were transferred into separate 10-mL aliquots of tryptic soy broth (TSB). These cultures were incubated at 30° C. for 18-24 h, with shaking at 150-200 rpm.

A volume of 10 mL of sterile phosphate buffer was measured out. The two mold strains were added by wetting sterile swabs in phosphate buffer, or water, and then rolling the swabs over the molds, covering an area of approximately 1 $in^2$ on each plate. The mold-covered swabs were then immersed in the 10 mL of phosphate buffer and agitated to suspend the spores. A volume of 0.1 mL of each bacterial culture, and a volume of 1 mL of each yeast culture, was then added to the mold mixture. The inoculum was blended by vortexing briefly. The organisms used in the inoculum and their corresponding American Type Culture Collection numbers (ATCC #) are shown in Table 1.

TABLE 1

Contents of Standard Industrial Inoculum

| Microorganism | ATCC # |
|---|---|
| Gram Negative Bacteria | |
| Pseudomonas aeruginosa | 10145 |
| Pseudomonas putida | 12633 |
| Enterobacter aerogenes | 13048 |
| Alcaligenes faecalis | 25094 |
| Proteus vulgaris | 13315 |
| Burkholderia cepacia | 21809 |
| Pseudomonas fluorescens | 13525 |
| Yeast | |
| Saccharomyces cerevisiae | 2338 |
| Candida lipolytica | 18942 |

TABLE 1-continued

Contents of Standard Industrial Inoculum

| Microorganism | ATCC # |
|---|---|
| Mold | |
| *Aspergillus niger* | 6275 |
| *Penicillium ochrochloron* | 9112 |

Samples were inverted several times to mix in the microorganisms. This inoculation challenged each test sample with $10^6$-$10^7$ colony forming units/mL latex. Using a 10-µL sterile loop, latex samples were streaked onto tryptic soy agar (TSA) plates. This procedure was carried at t=0 and at several other time points during the first ~5 h of the experiment to obtain speed-of-kill data. Additional time points were taken at t=1, 2 and 7 days. Between time points, all samples were stored at 30° C. In addition, all streaked TSA plates were incubated at 30° C. Normally, plates were rated for microbial growth following 48 h of incubation. The growth rating system for challenge tests is illustrated in Table 2 and the summary of the results for preservative efficacy testing is shown in Table 3.

TABLE 2

Rating System for Challenge Testing

| Number of Colonies on Plate | Rating Score | Estimated Colony Forming Units/mL | Contamination |
|---|---|---|---|
| None | 0 | <$10^2$ | None |
| <10 | Tr | $10^2$-$10^3$ | Trace |
| 10 to 100 | 1 | $10^3$-$10^4$ | Very Light |
| 100 to 1000 | 2 | $10^4$-$10^5$ | Light |
| 1000 to 10,000 | 3 | $10^5$-$10^6$ | Moderate |
| >10,000 | 4 | >$10^6$ | Heavy |

TABLE 3

Results for Preservative Efficacy Testing

| | | Growth Ratings | | | | | | |
|---|---|---|---|---|---|---|---|---|
| Sample (Dosages b/f Heat-Aging) | KATHON (ppm) | t = 0 h | t = 2 h | t = 3.5 h | t = 5 h | t = 24 h | t = 48 h | t = 168 h |
| Comp. Ex. 1 | 7.8 | 4 | 2 | 1 | Tr | 0 | 0 | 0 |
| Ex. 1 (2350 ppm 14 mM) | NA | 4 | 0 | 0 | 0 | 0 | 0 | 0 |
| Ex. 2 (2350, 14 mM) | 8.3 | 1 | 0 | 0 | 0 | 0 | 0 | 0 |
| Ex. 3 (940, 6 mM) | 8.0 | 4 | 1 | Tr | 0 | 0 | 0 | 0 |
| Ex. 4 (1900 ppm, 14 mM) | 8.0 | 3 | 0 | 0 | 0 | 0 | 0 | 0 |

The data show that Cl-TOA is effective as a quick-kill preservative alone or in combination with the KATHON™ LX Microbicide. The heat-age treatment of the samples of Examples 1-3, which simulates a 4-month storage of binder, demonstrates that Cl-TOA was still efficacious even though its concentration had dropped from 2350 ppm to ~160 ppm for samples 1 and 2 (as determined by GC analysis) and to ~65 ppm for Example 3. Example 4 is provided to show that although TOA has little or no biocidal activity, it is effective as an adjuvant for the biocide as demonstrated by its superior performance as compared to the microbiocide alone (Comp. Ex. 1). Accordingly, because it is known from GC data that Cl-TOA decomposes, in part, to form TOA, the Cl-TOA is effective both as a biocide and, through decomposition, as an adjuvant.

The invention claimed is:

1. A process comprising contacting a sufficient amount of a halamine with a latex binder to achieve microbial prophylaxis, wherein the halamine is characterized by the following formula:

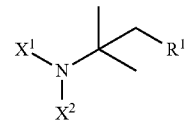

wherein $X^1$ is H, Br, or Cl; $X^2$ is Br or Cl; and $R^1$ is H or a $C_{1-30}$ alkyl group or mixtures thereof.

2. The process of claim 1 wherein the halamine is added as an emulsified dispersion at a level 10 ppm to 1 weight percent, based on the volume of latex; $X^1$ is H or Cl; and $X^2$ is Cl.

3. The process of claim 2 wherein $R^1$ is a $C_{4-20}$ alkyl group or mixtures thereof or a —$C(CH_3)_3$ group.

4. The process of claim 1 wherein a non-halamine biocide is added to the latex binder prior to, concurrent with, or subsequent to contacting the halamine with the latex.

5. The process of claim 4 wherein the non-halamine biocide is an isothiazolone.

6. The process of claim 5 wherein the isothiazolone is 5-chloro-2-methyl-4-isothiazolin-3-one or 2-methyl-4-isothiazolin-3-one or a combination thereof.

7. A composition comprising a latex binder and a halamine characterized by the following formula:

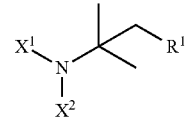

wherein $X^1$ is H, Br, or Cl; $X^2$ is Br or Cl; and $R^1$ is H or a $C_{1-30}$ alkyl group or mixtures thereof.

8. The composition of claim 7 which further includes a non-halamine biocide; wherein $R^1$ is —$C(CH_3)_3$ or a $C_{8-20}$ alkyl group; $X^1$ is H or Cl and $X^2$ is Cl.

9. The composition of claim 8 wherein the non-halamine biocide is an isothiazolone; and $R^1$ is —$C(CH_3)_3$.

10. The composition of claim 7 which further includes a hindered primary amine characterized by the following structure:
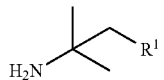
wherein $R^1$ is H or a $C_{1-30}$ alkyl group or mixtures thereof.
* * * * *